United States Patent [19]

Fong

[11] Patent Number: 5,320,530
[45] Date of Patent: Jun. 14, 1994

[54] ENDODONTIC APPARATUS FOR RETROFILL CAVITY PREPARATION

[76] Inventor: Cheng D. Fong, 60 Haven Ave., New York, N.Y. 10032

[21] Appl. No.: 992,074

[22] Filed: Dec. 17, 1992

[51] Int. Cl.⁵ .............................................. A61C 1/07
[52] U.S. Cl. ...................................... 433/119; 433/165
[58] Field of Search .............. 433/102, 118, 119, 124, 433/127, 133, 141, 142, 146, 147, 165, 81

[56] References Cited

U.S. PATENT DOCUMENTS

| | | | |
|---|---|---|---|
| 322,265 | 7/1885 | Donaldson | 433/102 |
| 735,580 | 8/1903 | Phillips | 433/147 X |
| 873,100 | 12/1907 | Skalstad | 433/102 |
| 3,471,929 | 10/1969 | Boone | 433/147 X |
| 3,995,372 | 12/1976 | Rapuano | 32/40 |
| 4,071,029 | 1/1978 | Richmond et al. | 433/133 |
| 4,229,168 | 10/1980 | Scholz, Jr. | 433/124 |
| 4,552,531 | 11/1985 | Martin | 433/141 X |
| 4,738,616 | 4/1988 | Reynaud | 433/220 |
| 4,834,653 | 5/1989 | Edwardson | 433/118 |
| 4,840,566 | 6/1989 | Leonard | 433/127 |
| 4,992,048 | 2/1991 | Goof | 433/102 |
| 5,094,617 | 3/1992 | Carr | 433/119 |
| 5,100,321 | 3/1992 | Coss | 433/118 |
| 5,133,661 | 7/1992 | Euvrard | 433/120 |

OTHER PUBLICATIONS

Catalog of Medidenta International, Inc., Woodside, N.Y. 11377, Fall/Winter 1985/1986, Cover Page and p. 2.

Osada Electric Co. Inc., Los Angeles, Calif. (Advertisement).
Amadent, Cherry Hill, N.J. (Advertisement).
Excellence in Endodontics, San Diego, Calif. (Advertisement in Journal of Endodontics, Oct. 1992).

*Primary Examiner*—Gene Mancene
*Assistant Examiner*—Nicholas D. Lucchesi
*Attorney, Agent, or Firm*—Darby & Darby

[57] ABSTRACT

An endodontic tool has a working tip including two cylindrical segments connected together lengthwise and terminating in a conical tip. The cylindrical segment which connects directly to the conical tip is smaller in diameter than the second cylindrical segment, whereby a shoulder is provided at the intersection of the two cylindrical segments. The conical tip and first cylindrical segment have surfaces for removing tooth material when the tool is vibrated at sonic frequencies. A stem connects to the second cylindrical segment at a right angle and is connectable to a conventional sonic hand piece so that vibratory energy generated within the hand piece is transmitted to the working tip by way of the stem. The hand piece provides vibratory motion generally along its longitudinal axis, and the stem is received in the hand piece with the stem axis at an angle to the longitudinal axis of the hand piece. The stem can be rotated about its own axis in the hand piece such that orientation of the working tip relative to the longitudinal axis of the hand piece is readily and releasably adjustable.

24 Claims, 2 Drawing Sheets

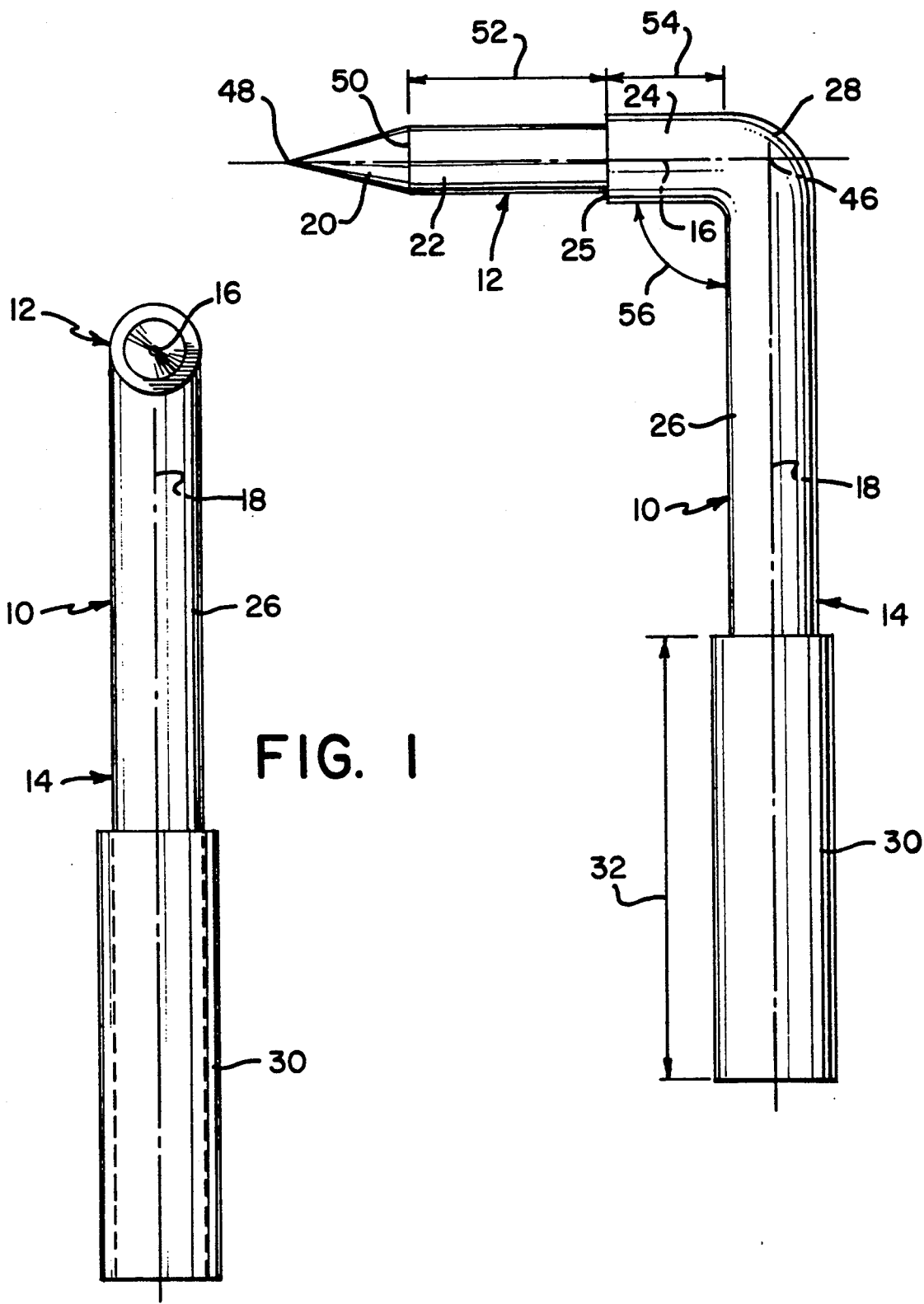

ENDODONTIC APPARATUS FOR RETROFILL CAVITY PREPARATION

BACKGROUND OF THE INVENTION

This invention relates generally to dental apparatus for use in endodontic procedures and more particularly to a tool and hand piece suitable for retrofill cavity preparation, that is, preparation of a root cavity for filling from the bottom, by access through an opening provided in the jawbone.

In root canal surgery, the space containing the pulp is opened by drilling into the tooth from the top. The pulp is then removed and a suitable material is used to fill the entire internal volume of the tooth. However, if pain persists or if problems develop subsequently to cause the patient to feel pain in the tooth, it may be necessary to drill into the bottom of the tooth root which is seated in the jawbone. Such drilling is accomplished from the side, through the gums and jawbone. The tip or bottom of the root is removed and the bottom of the root canal is bored out and is subsequently filled with a filler material.

In the past, such bore has been made by an vibratory instrument operating at ultrasonic frequencies. Vibrations are induced in the tool by a mechanism, typically including a piezoelectric element, in a hand piece to which the tool is mounted, and which is adapted to be held by the dental surgeon. Rotary drilling bits are also sometimes used in place of, or in conjunction with, tools operating with vibratory motion. Because of the various locations in the mouth where root canal surgery may be required and because of the relative inaccessibility of many of these areas and the small space between cheek and jawbone, tools of many different shapes have been constructed to accommodate the various tooth locations so that the bottom of the root can be reached for retrofill cavity preparation regardless of the tooth's location. No single tool is known which is sufficiently versatile to operate at all of the tooth locations. Many possibilities for misaligning a drilled cavity, or for overenlargement or excessive depth of a drilled cavity, are present. Such hazards are especially prevalent when using devices that vibrate at ultrasonic frequencies, since a small deviation from an intended path of operation can quickly and undesirably remove relatively large quantities of tooth material. Among others, the risk of an unintended breaking through of the side wall of a tooth is increased at ultrasonic frequencies. At best, operation of these tools involves very delicate and time consuming procedures.

Further, when operating at ultrasonic speeds with conventional tools, it is difficult to avoid enlarging the entrance to the cavity drilled at the bottom of the root such that the cavity becomes conical in shape, that is, increasing in diameter toward the bottom of the root. Such a conical shape, when filled from the bottom, results in a filling which may easily be dislodged. A straight, i.e. cylindrical, bore into the bottom of the tooth is preferred, since the friction from the parallel side wall of the bore aids in maintaining the filler material in place.

In the prior art, U.S. Pat. No. 5,094,617, issued Mar. 10, 1992, provides an ultrasonic tool having a conical working end that is connected at an angle to an elongated stem. Stems of many different shapes, both smoothly curved and also bent at clearly defined angles, are disclosed. Regardless of shape, the stem is received coaxially in a compatible tool holder of a hand piece for a dental retrofill instrument. Longitudinal ultrasonic vibrations generated in the hand piece are transmitted to the stem and to the conical working end of the tool, which is applied to a patient's tooth. The above-mentioned hazards associated with ultrasonic tools affect usage of the tools of the type disclosed in U.S. Pat. No. '617. The need for numerous tools, each of a different shape so as to access teeth of different locations can be an inconvenience to the surgeon.

SUMMARY OF THE INVENTION

It is an object of the invention to provide an improved endodontic tool for retrofill cavity preparation that operates in a conventional sonic hand piece using conventional air and water inputs currently available at modern dental offices.

Another object of the invention is to provide an improved endodontic tool for retrofill cavity preparation, that is small in size and capable of adjustable installation in a hand piece so as to enable a single tool to be used at a multitude of different tooth locations.

A further object of the invention is to provide an improved endodontic tool for retrofill cavity preparation that reduces the hazards of unintentional removal of tooth material associated with ultrasonic tools.

Still another object of the invention is to provide an improved endodontic tool for retrofill cavity preparation which is an efficient tooth material removing device and will enlarge the lower portion of the root canal in generally cylindrical shape.

Yet another object of the invention is to provide an improved endodontic tool for retrofill cavity preparation that is not only versatile but is simple to manufacture and economical to produce.

An endodontic tool in accordance with the invention has a working tip including two coaxial cylindrical segments connected together lengthwise and terminating in a conical tip. The cylindrical segment which connects directly to the conical tip is smaller in diameter than the second cylindrical segment, whereby a shoulder is provided at the intersection of the two cylindrical segments. The shoulder limits or gives indication of the depth of drilling into the tooth root. The conical tip and first cylindrical segment have surfaces that are suitable for removing tooth material when the tool is vibrated at sonic frequency and placed into contact with a tooth surface.

A stem connects at one end to the second cylindrical segment at a substantially right angle with respect to the lengthwise extension of the working tip. The stem is connectable at its other end to a conventional sonic hand piece of, for example, the type used for cleaning teeth, so that vibratory energy generated within the hand piece is transmitted to the tool, that is, to the working tip, by way of the stem. The hand piece provides vibratory motion generally along its longitudinal axis, and the stem is received in the hand piece with the stem axis at an angle to the longitudinal axis of the hand piece. The stem can be rotated, about its own axis, in the hand piece such that orientation of the working tip relative to the longitudinal axis in the hand piece is readily and releasibly adjustable.

The shoulder provided between the two cylindrical segments on the working tip gives an indication to the surgeon of the extent of tool entry into the root cavity when drilling. Operation at sonic frequencies, as compared to ultrasonic, makes the tool much easier and safer to use. Accordingly, the risk of unintended removal of tooth material, break-through at the side walls of the tooth, and unintended enlargement at the entrance to the drilled cavity, is substantially reduced. Because the tool operates at lower vibrational frequency, when deviations from an intended path do occur, the risk of unintended removal of tooth material is substantially less than when operating with ultrasonic devices.

The tool in accordance with the invention is simple in shape and construction and, accordingly, is inexpensive to produce. It can operate on conventional sonic equipment using standard air and water connections available at the site of all modern dental chairs; no special accessories or tool holders are required to drive the tool.

Further objects and advantages of the invention will be apparent from the following detailed description and drawings. The invention accordingly comprises the features of construction, combination of elements, and arrangement of parts which will be exemplified in the constructions hereinafter set forth, and the scope of the invention will be indicated in the claims.

BRIEF DESCRIPTION OF THE DRAWING

For a fuller understanding of the invention, reference is had in the following description to presently preferred embodiments, taken in connection with the accompanying drawings, in which:

FIG. 1 is a front elevational view of an endodontic tool in accordance with the invention;

FIG. 2 is a side elevational view of the tool of FIG. 1; and

DESCRIPTION OF THE PREFERRED EMBODIMENTS

Figure 3:
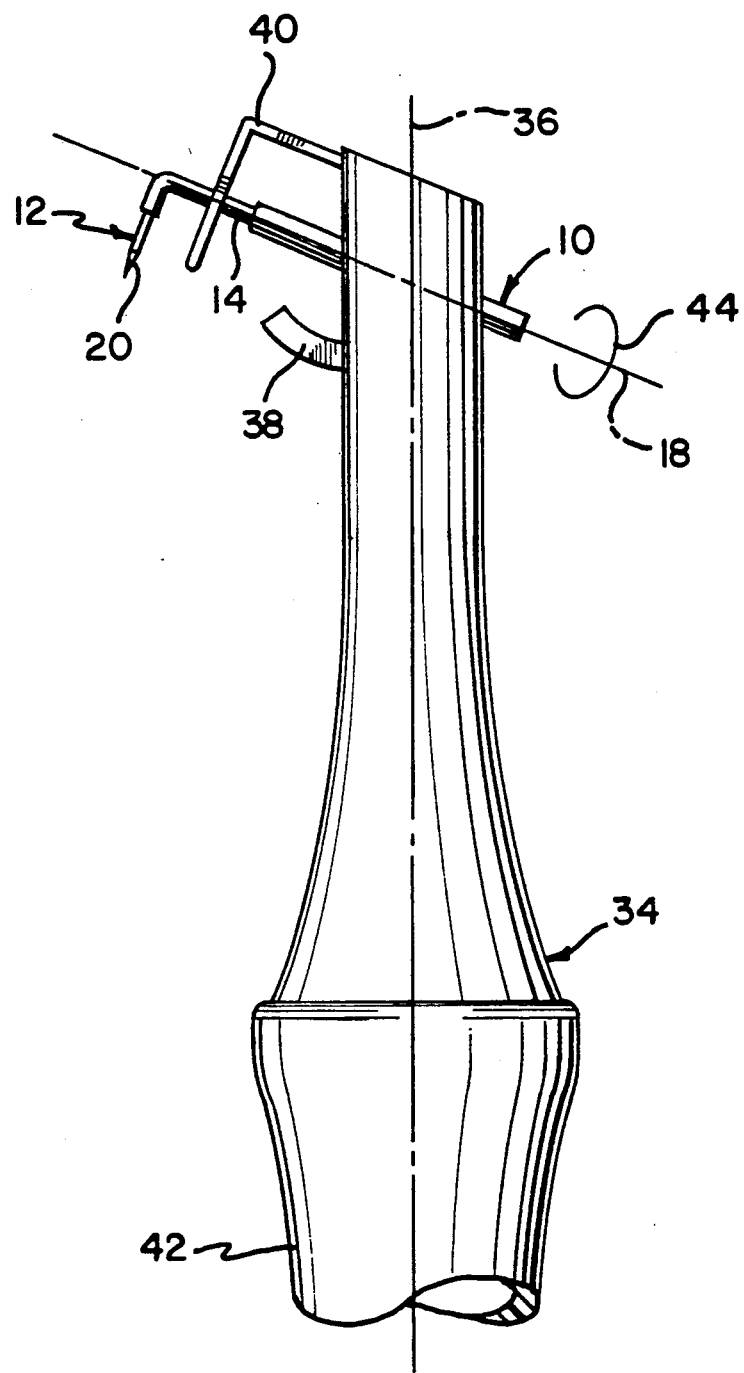
FIG. 3 illustrates the tool of FIGS. 1,2 mounted for use in a hand piece.

With reference to the figures, a tool 10 includes a working tip 12 that is connected to a stem 14 of extended length. The axis 16 of the working tip 12 intersects the axis 18 of the stem 14 at an angle of approximately 90°.

The working tip 12 includes a conical end 20 connected to a first cylindrical segment 22, which, in turn, is connected to a second cylindrical segment 24 of larger radius, whereby a shoulder 25 is formed. The conical end 20, and cylindrical segments 22,24 are centered on the tip axis 16.

The stem 14 includes a shaft 26 that is joined to the end of the working tip 12 via a curved intermediate portion 28 so as to avoid injuries to the patient as the tool is maneuvered in use in the oral cavity. A resilient sleeve 30 covers a lower portion 32 of the shaft 26. The lower stem portion 32 is used in engaging the working end, or tool holder, 34 of a hand piece 42 (FIG. 3), as discussed hereinafter.

The tool holder 34 is conventional, that is, presently available on the market, although a special tool holder may be constructed for use with the tool 10 of the present invention. For example, the tool 10 may be used in an MM1500 hand piece (Sonic Air MM1500Endo System, marketed by Micro-Mega, Woodside, New York). This is a device intended for use at sonic frequencies.

However, it should be understood that the working tip 12 in accordance with the invention is not limited for use with any particular tool holder. The tip 12 can be connected to any stem 14 that is particularly constructed for connection to other commercially available tool holders that are capable of providing proper vibratory motions in desired magnitudes and directions. It is only necessary that the lower portion 32 of the stem 14 be constructed, with or without the sleeve 30, to coöperate with the fastening means of the particular tool holder. The stem 14, with the resilient sleeve 30, has cooperated satisfactorily with the tool holder by Micro-Mega, mentioned above.

The axis 18 of the stem is positioned transversely to the longitudinal axis 36 of the tool holder 34 when the tool 10 is mounted to the tool holder. The two axes, 16, 18 of the working tip 12 and stem 14 are coplanar. Thus, the tool 10 can be rotated about the stem axis 18 to any orientation relative to the longitudinal axis 36 of the tool holder 34 before the tool 10 is tightened into position. The tool 10 is therefore readily positionable for convenient operation on any tooth in the mouth.

The tool holder of FIG. 3 also includes a nozzle 38 to provide coolant water for the tool 10 if required, and a guard 40 that encircles the stem 14 of the tool 10. These elements are not novel portions of the invention and accordingly are not discussed in detail herein.

FIG. 3 illustrates the tool 10 mounted with the working tip 12 lying in a common plane with the axes 18,36, with the conical end 20 pointing back, in the general direction of the hand piece 42, where the assembly is gripped by the surgeon when using the device. As noted above, the tool 10 can be rotated about the stem axis 18, as indicated by the arrow 44, before the tool 10 is locked into position on the tool holder 34 for use. Thus, the conical end 20 can be pointed upward (FIG. 3) or at any angle relative to the axis 18, and lie in or out of the plane of FIG. 3.

The tool 10 is made of any material having biological compatibility and sufficient strength for use in endodontic work, for example, stainless steel. The external surfaces of the working tip 12 need not be specially formed in manufacture in order to abrade tooth material. It is sufficient that the surface of the working tip 12 is not polished. For example, a useful tool can be turned from stainless steel on a lathe and then bent to shape, without polishing. Vibratory forces provided along the longitudinal axis 36 of a tool holder and acting transversely to the axis 18 of the stem have provided suitable energy, for the purposes described herein, to the working tip 12 of such a tool in clinical testing, irrespective of the angular position of the axis 16 of the tip 12 with respect to the axis 36.

In a tool 10 that has performed satisfactorily, the length of the conical end 20 from the apex 48 to the base 50 of the cone is in a range of approximately 0.5 to 2.0 millimeters. The length of the first cylindrical segment 22 is in a range of approximately 1.5 to 3 millimeters. The length 54 of the second cylindrical segment 24 is in a range of approximately 1 to 3 millimeters. The radius of the first cylindrical segment 22 is in a range of approximately 0.1 to 0.5 millimeters and the radius of the second cylindrical segment 24 is in a range of approximately 0.3 to 0.8 millimeters. The shaft 26 has approximately the same radius as the second cylindrical segment 24. The outside radius of the resilient sleeve 30 is in a range of approximately 0.8 millimeters to 1.2 millimeters. The angle 56 between the working tip axis 16 and the stem axis 18 is in a range of approximately 90° plus or minus 10°.

Tests of the tool 10 were performed using conventional sonic hand pieces, as indicated above, to confirm that the energy levels produced by such conventional sonic instruments, which energy levels are lower than those of comparable ultrasonic instruments, were not only sufficient for cavity preparation with the tool tip of the instant invention but further, allowed such preparation with less risk to the patient, easier handling for the dental surgeon and better long term adhesion of the filling material. The tool assembly including the tool 10 and hand piece 42 operated with conventional inputs of air and water. It was possible to obtain a deep preparation, which followed the original path of the apical root canal. Because of the small size of the tool 10, it was found in clinical tests that the tooth apices were easily accessible to the MM1500 hand piece, and removal of peri-apical bone was either not necessary or could be kept at a minimum.

The shoulder 25, produced by the different diameters of the first and second cylindrical segments 22,24 of the working tip 12, prevented working to excessive depth in the tooth. The straight cylindrical contour of the first cylindrical segment 22 allowed the formation of a cylindrical rather than a conical cavity in the bottom of the tooth root. This provides increased friction and thus better retention of the filler material which is inserted from the bottom of the tooth cavity. The conical end 20 was highly effective in leading the tool into the cavity and in removal of filler material that remained from earlier endodontic procedures. Because of the lower energy levels in the sonic device and because of the small size and adjustability of the tool 10, a fine, well-formed, cylindrical, cavity preparation can be made without removal of an excessive amount of tooth of material.

It will thus be seen that the objects set forth above, and those made apparent from the preceding description, are efficiently attained and, since certain changes may be made in the above constructions without departing from the spirit or the scope of the invention, it is intended that all matter contained in the above description, or shown in the accompanying drawings shall be interpreted as illustrative and not in a limiting sense.

What is claimed is:

1. An endodontic apparatus for retrofill cavity preparation, comprising:
   a tool including a working tip having a first axis, said tip including a generally conical end connected to one end of a first cylindrical segment, and a second cylindrical segment connected to the other end of said first cylindrical segment, the cross section of said second cylindrical segment being larger than the cross section of said first cylindrical segment to form a shoulder at the juncture of said first and second cylindrical segments, said cylindrical segments and said conical end being aligned to said first axis, the outer surfaces of both said conical end and said first cylindrical segment being working surfaces for acting on a tooth and for removing tooth material; and
   a stem for connection to a tool holder and having a first end and a second end, said second end being connected to said second cylindrical segment at the end of said second cylindrical segment away from said first cylindrical segment said stem being selectively positionable about a second axis when said stem is connected to said tool holder.

2. An endodontic apparatus as in claim 1, further comprising a tool holder having a length and connection means for releasibly gripping said stem, said tool holder including dynamic means for providing vibrations at least along a lengthwise third axis, said vibrations being transmitted to said working tip via said stem when said stem is gripped by said connection means, said second axis and said third axis intersecting at an angle.

3. An endodontic apparatus as in claim 2, wherein said first and second axes meet at an angle.

4. An endodontic apparatus as in claim 3, wherein said connection means, when released, permit rotation of said stem about said second axis, whereby the orientation of said working tip relative to said tool holder is adjustable.

5. An endodontic apparatus as in claim 2, wherein said dynamic means provides vibrations at frequencies in the sonic range.

6. An endodontic apparatus as in claim 2, further comprising a resilient sleeve, a portion of said stem being encircled in said sleeve in a region where said tool is gripped by said tool holder in use.

7. An endodontic apparatus as in claim 1, wherein said first and second axes meet at an angle.

8. An endodontic apparatus as in claim 1, wherein said stem is cylindrical and has said second axis at its center.

9. An endodontic apparatus as in claim 1, wherein the base of said generally conical end is circular and said cylindrical segments are circular in cross section.

10. An endodontic apparatus as in claim 1, wherein said first axis and said second axis intersect at substantially a right angle.

11. An endodontic apparatus as in claim 1, wherein said conical end has a length from the apex to the base of said end in a range of approximately 0.5 to 2.0 millimeters and said base has a radius in a range of approximately 0.1 to 0.5 millimeters.

12. An endodontic apparatus as in claim 1, wherein said first cylindrical segment has a length in a range of approximately 1.5 to 3.0 millimeters and a radius in a range of approximately 0.3 to 0.8 millimeters.

13. An endodontic apparatus as in claim 1, wherein said second cylindrical segment has a length in a range of approximately 1.0 to 3.0 millimeters and a radius in a range of approximately 0.3 to 0.8 millimeters.

14. An endodontic apparatus as in claim 1, wherein the length of said stem is in a range of approximately 20 to 30 millimeters and the radius of said stem is in a range of approximately 0.8 to 1.2 millimeters.

15. An endodontic apparatus as in claim 1, further comprising a resilient sleeve, and wherein said stem is round and has a radius in a range of approximately 0.3 to 0.8 millimeters and is encircled with said resilient sleeve at one end, said sleeve having an outer radius in a range of approximately 0.8 to 1.2 millimeters.

16. An endodontic apparatus as in claim 1, wherein said shoulder includes a planar surface which is generally perpendicular to said first axis.

17. An endodontic apparatus as in claim 1, wherein a short axial length of said conical end is such that said working surface of said first cylindrical segment contacts tooth material after shallow penetration of a tooth by said conical end.

18. An endodontic apparatus as in claim 17, wherein the axial length of said conical end is in the range of approximately 15 percent of 55 percent of the distance from an apex of said conical end to said shoulder.

19. An endodontic apparatus as in claim 1, wherein said conical end has a length from the apex to the base of said conical end in a range of approximately 0.5 to 2.0 millimeters and said first cylindrical segment has a length in a range of approximately 1.5 to 3.0 millimeters.

20. An endodontic apparatus for retrofill cavity preparation, comprising:

a working tip having a first axis, said tip including a generally conical end connected to one end of a cylindrical segment, said cylindrical segment and said conical end being aligned to said first axis, the outer surface of said conical end and the outer surface of said cylindrical segment being working surfaces for acting on a tooth and for removing tooth material;

a stem having a first end and a second end, said second end being connected to said cylindrical segment at the end of said cylindrical segment away from said conical end, a second axis extending linearly between said first and second ends of said stem, said first and second axes meeting at an angle of approximately 90°; and an elongated hand piece having connection means for releasibly gripping said stem, said hand piece including dynamic means for providing sonic vibrations at least along a third axis lengthwise of said hand piece, said sonic vibrations being transmitted to said working tip via said stem when said stem is gripped by said connection means, said second axis and said third axis intersecting at an angle.

21. An endodontic apparatus as in claim 20, further comprising a resilient sleeve, a portion of said stem being encircled in said sleeve in a region where said stem is gripped by said hand piece in use.

22. An endodontic apparatus as in claim 20, wherein said first axis and an apex of said conical end face in a direction generally towards the hand piece.

23. An endodontic apparatus as in claim 20, wherein said working tip vibrates in a complex mode generally parallel to said third axis and toward and away from said hand piece.

24. An endodontic apparatus as in claim 20 wherein said stem includes an elbow portion.

* * * * *